United States Patent
Buckner, III et al.

(10) Patent No.: US 6,393,900 B1
(45) Date of Patent: May 28, 2002

(54) AEROSOL CAN CONTENT ANALYZER WORKSTATION

(75) Inventors: Charles Amick Buckner, III, Durham; Jeffrey Scott Thomas, Erwin, both of NC (US)

(73) Assignee: SmithKline Beecham Corporation, Philadelphia, PA (US)

( * ) Notice: Subject to any disclaimer, the term of this patent is extended or adjusted under 35 U.S.C. 154(b) by 0 days.

(21) Appl. No.: 09/441,904

(22) Filed: Nov. 17, 1999

(51) Int. Cl.$^7$ .......................... G01N 1/00; B65B 31/00; B67D 5/00
(52) U.S. Cl. ................. 73/61.56; 73/864.81; 141/51; 141/7; 222/86
(58) Field of Search .................. 73/31.05, 61.56, 73/52, 864.81, 864.85, 864.87, 23.2, 61.57; 141/1, 51, 7, 97; 100/45, 98 R; 134/167 R; 137/341; 222/86; 702/22

(56) References Cited

U.S. PATENT DOCUMENTS

| | | | | |
|---|---|---|---|---|
| 4,058,412 A | * | 11/1977 | Knapp et al. ................. 134/24 |
| 4,096,734 A | | 6/1978 | Khayat |
| 4,274,453 A | * | 6/1981 | Lee ................................ 141/1 |
| 4,300,909 A | * | 11/1981 | Krumhansl .................... 436/50 |
| 4,364,263 A | * | 12/1982 | Sankoorikal et al. ....... 73/61.56 |
| 4,407,341 A | * | 10/1983 | Feldt et al. .................... 141/97 |
| 4,459,906 A | * | 7/1984 | Cound et al. .................. 100/45 |
| 4,944,333 A | * | 7/1990 | Gold et al. .................... 141/51 |
| 4,961,440 A | * | 10/1990 | Wright .................... 134/167 R |
| 5,067,529 A | * | 11/1991 | Gonzalez-Miller et al. .... 141/7 |
| 5,114,043 A | * | 5/1992 | Collins, Jr. ................... 222/86 |
| 5,166,889 A | * | 11/1992 | Cloyd ........................... 702/22 |
| 5,181,462 A | * | 1/1993 | Isaac ........................ 100/98 R |
| 5,199,297 A | | 4/1993 | Lin et al. |
| 5,261,538 A | | 11/1993 | Evans et al. |
| 5,270,211 A | * | 12/1993 | Kelln et al. .................... 436/43 |
| 5,271,437 A | * | 12/1993 | O'Brien et al. ............... 141/51 |
| 5,279,337 A | | 1/1994 | Ringet et al. |
| 5,309,956 A | * | 5/1994 | Hajma ............................ 141/7 |
| 5,332,009 A | * | 7/1994 | Van Etten ....................... 141/7 |
| 5,365,982 A | * | 11/1994 | O'Neill ......................... 141/51 |
| 5,385,177 A | * | 1/1995 | O'Neill .......................... 141/1 |
| 5,529,097 A | * | 6/1996 | Campbell ..................... 141/51 |
| 5,615,715 A | * | 4/1997 | Yore ............................. 141/51 |
| 5,694,973 A | * | 12/1997 | Chordia ....................... 137/341 |
| 5,988,211 A | * | 11/1999 | Cornell ....................... 137/504 |

FOREIGN PATENT DOCUMENTS

| | | |
|---|---|---|
| DE | 2350734 A1 | 4/1975 |
| EP | 03 09 122 A2 | 3/1989 |
| FR | 2711803 A1 | 5/1995 |

* cited by examiner

*Primary Examiner*—Hezron Williams
*Assistant Examiner*—Jay L. Politzer
(74) *Attorney, Agent, or Firm*—James P. Riek

(57) ABSTRACT

An aerosol can content analyzer workstation is disclosed which will make available the drug content of an aerosol can by a mechanical extraction process wherein the extraction is performed by isolating the bottom portion of the aerosol can in an extraction chamber. The aerosol can bottom is pierced by a metal punch after the aerosol can bottom is isolated. An extraction solvent is dispensed through spray holes in the metal punch in order to extract the contents from within the can. The extract is then collected in a collection flask and the extract is analyzed in order to determine the drug content.

50 Claims, 7 Drawing Sheets

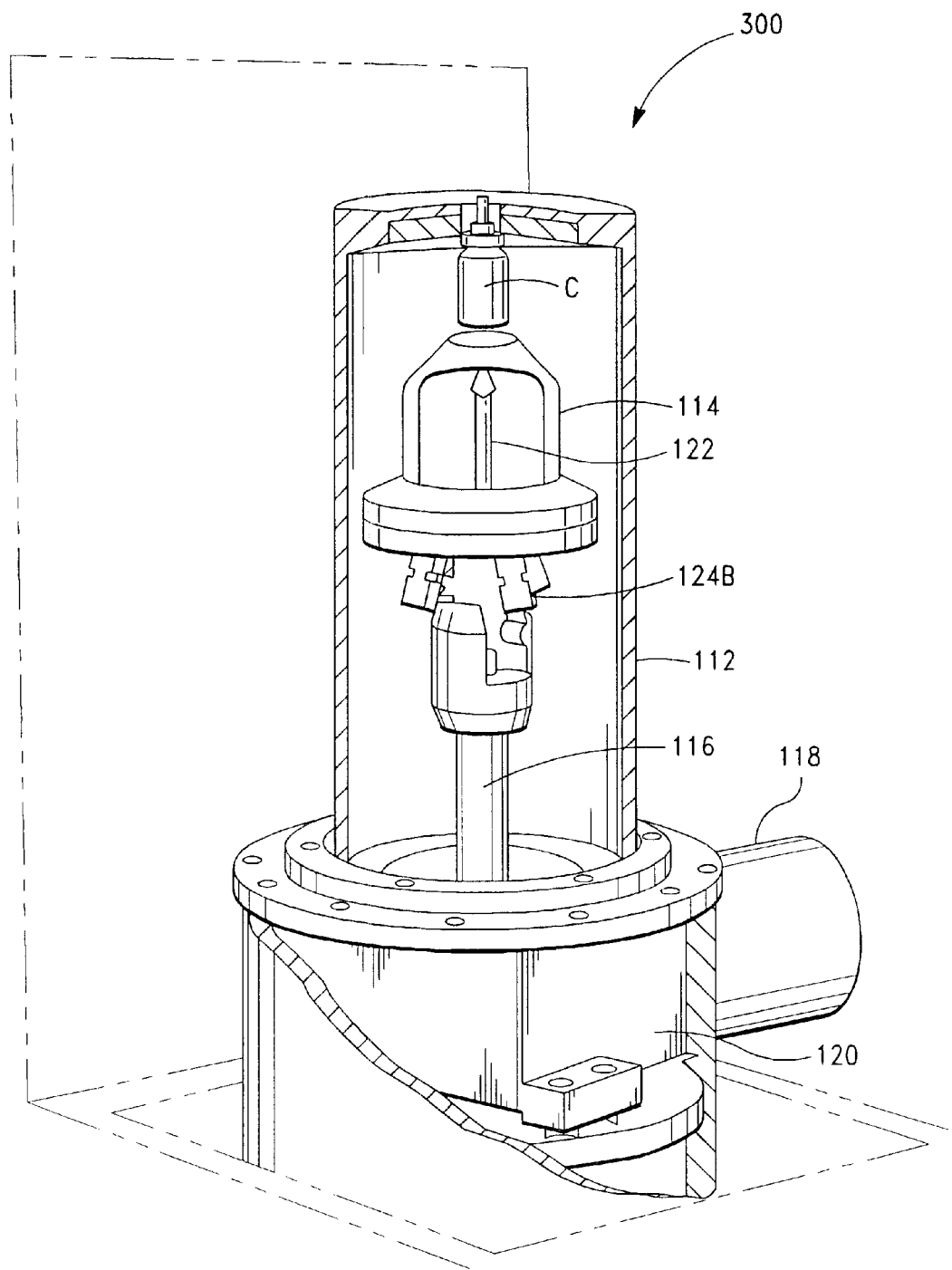
*FIG.—6A*

AEROSOL CAN CONTENT ANALYZER WORKSTATION

TECHNICAL FIELD

The present invention relates to aerosol can content testing, and more particularly relates to an automated system for performing aerosol can content testing.

RELATED ART

As is well known to those in the pharmaceutical industry involved in the selective testing of aerosol can contents required by regulations imposed by various government agencies (e.g., FDA), the drug product content testing of aerosol cans is currently performed manually by chilling the aerosol can and the contents thereof in a dry ice bath. After the contents of the aerosol can has been sufficiently chilled to reduce internal pressure, the aerosol can is then opened by a suitable cutting device such as a specialized electric can opener. The aerosol can is then placed into a glass flask and the propellant therein is allowed to evaporate from the open can. After the propellant has evaporated, the active drug is extracted utilizing a suitable solvent, such as methanol. Liquid handling is then performed on the extraction in order to ready the final sample to be analyzed by UV or HPLC, depending on the drug product. The UV or HPLC testing will determine the amount of drug content in the aerosol can being tested by a technician.

Although the manual testing currently being utilized is known to be effective, the testing requires an inordinate amount of time by a trained technician and that the test be performed at a temperature below the "boiling" point of the propellant. Thus, there is a long-felt need for an automated aerosol can content testing apparatus and method that can test aerosol cans for drug content in an accurate and time efficient manner and that avoids the necessity to use dry ice.

DISCLOSURE OF THE INVENTION

In accordance with the present invention, applicants provide an automated aerosol can content analyzer workstation to determine the drug content of a selected aerosol can. The aerosol can content analyzer workstation includes an extraction mechanism comprising an extraction chamber for receiving an aerosol can therein. A piercing element is positioned within the extraction chamber for piercing the aerosol can when the aerosol can is at ambient temperature.

In use, the present invention provides a method for analyzing the drug content of an aerosol can that includes placing the aerosol can in an extraction chamber wherein the extraction chamber is at ambient temperature. The method next provides for rupturing the aerosol can so as to allow the pressurized contents of the aerosol can to expel into the extraction chamber and then analyzing the contents of the aerosol can to determine the drug content.

It is therefore an object of the present invention to provide an aerosol can content analyzer workstation for use in determining the drug content of selected aerosol cans in a pharmaceutical testing procedure.

It is another object of the present invention to provide an procedure to replace the manual procedure presently used by pharmaceutical manufacturers for testing the aerosol can content so as to significantly expedite the testing procedure and to provide for more reliable testing results than the presently known manual aerosol can content testing procedure.

Some of the objects of the invention having been stated hereinabove, other objects will become evident as the description proceeds, when taken in connection with the accompanying drawings described below.

BRIEF DESCRIPTION OF THE DRAWINGS

FIG. 6A is a perspective view of the extraction mechanism of the workstation shown in FIG. 3 with the extraction chamber in its inoperative lowered position beneath an aerosol can.

BEST MODE FOR CARRYING OUT THE INVENTION

Referring now more specifically to the drawings, a preferred embodiment of the automated aerosol can content analyzer workstation in accordance with the present invention is shown in FIGS. 2–6 of the drawings and generally designated 100. It will be understood that automated aerosol can content analyzer workstation 100 was developed to make available the drug content of selected aerosol cans by an automated mechanical extraction process to be used in lieu of presently known manual processes wherein an aerosol can and its contents are chilled in a dry ice bath and subsequently opened and placed into glassware and the propellant therein allowed to evaporate. However, applicants wish to note that the aerosol can content analyzer apparatus and the method for analyzing the drug content of an aerosol can in accordance with the present invention can also be embodied in a manual apparatus and manual procedure, respectively, and that the manual embodiment of the apparatus and method of the present invention are both within the contemplated scope of the invention as described herein and as set forth in the claims appended hereto.

In the manual process, after the propellant has evaporated, the active drug is extracted utilizing a suitable solvent such as methanol. Liquid handling is then performed on the extraction to prepare the final sample to be analyzed by UV or HPLC, depending on the drug product. By contrast, applicants' automated aerosol can content analyzer workstation 100 performs the extraction by isolating the bottom portion of an aerosol can in an extraction chamber. The aerosol can bottom is then pierced by a metal punch immediately after the aerosol can bottom is isolated, and an extraction solvent such as methanol is dispensed through spray holes in the metal punch to extract the contents from within the can and allow them to collect in the extraction chamber. The extracted contents are then collected in a collection flask where further liquid handling steps occur in order to analyze the drug content of the aerosol can.

Figure 2A:
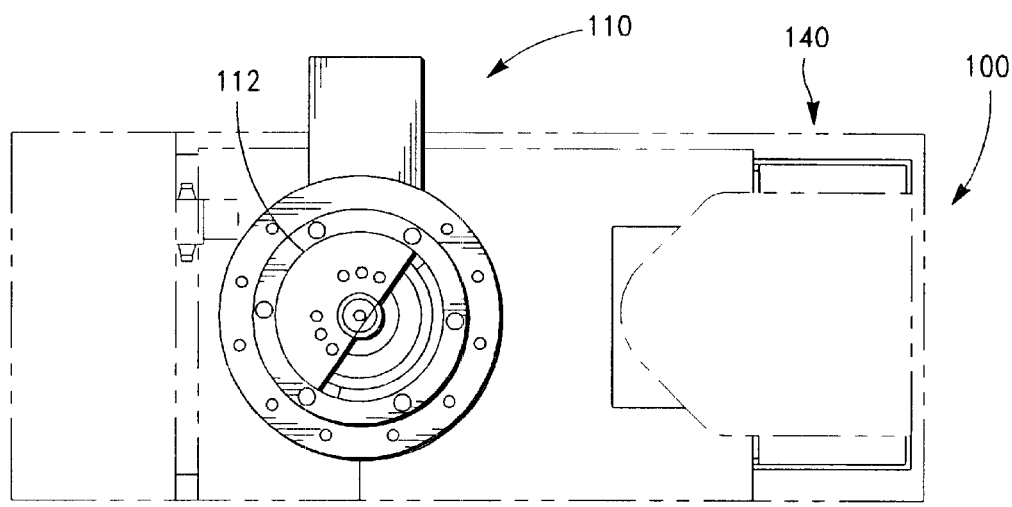
FIG. 2A is a top plan view of the automated aerosol can content analyzer workstation of the present invention.
Figure 2B:
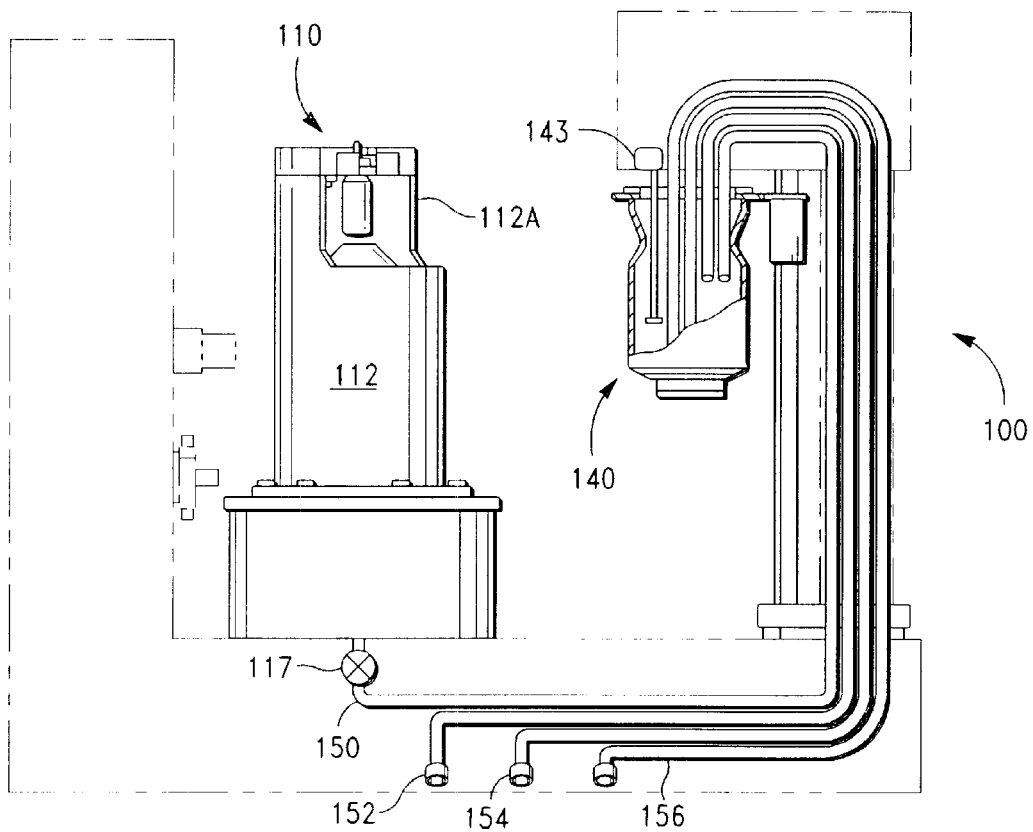
FIG. 2B is a side elevation of the automated aerosol can content analyzer workstation of the present invention.
Figure 3:
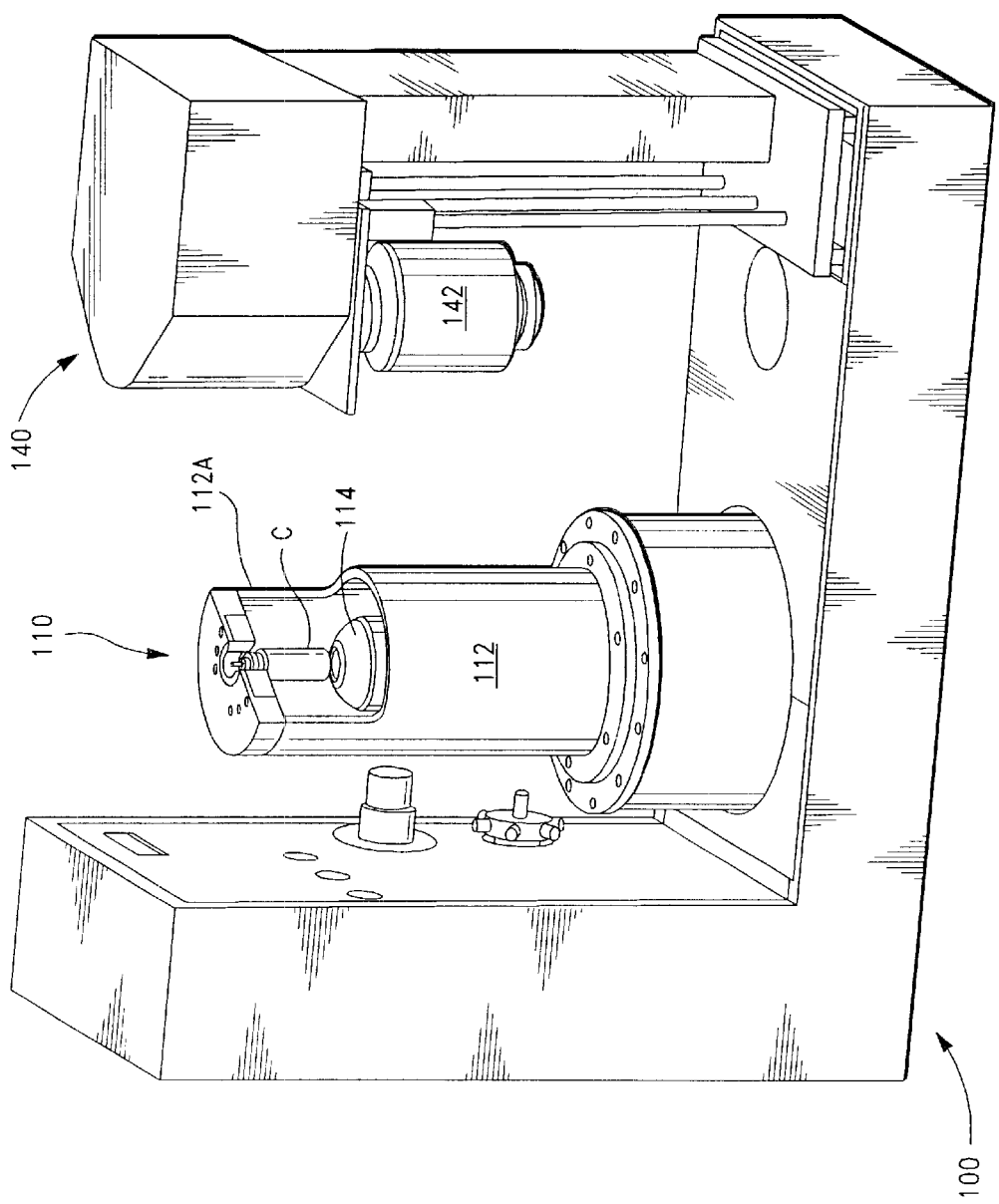
FIG. 3 is a perspective view of the automated aerosol can content analyzer workstation of the present invention.
Figure 4:
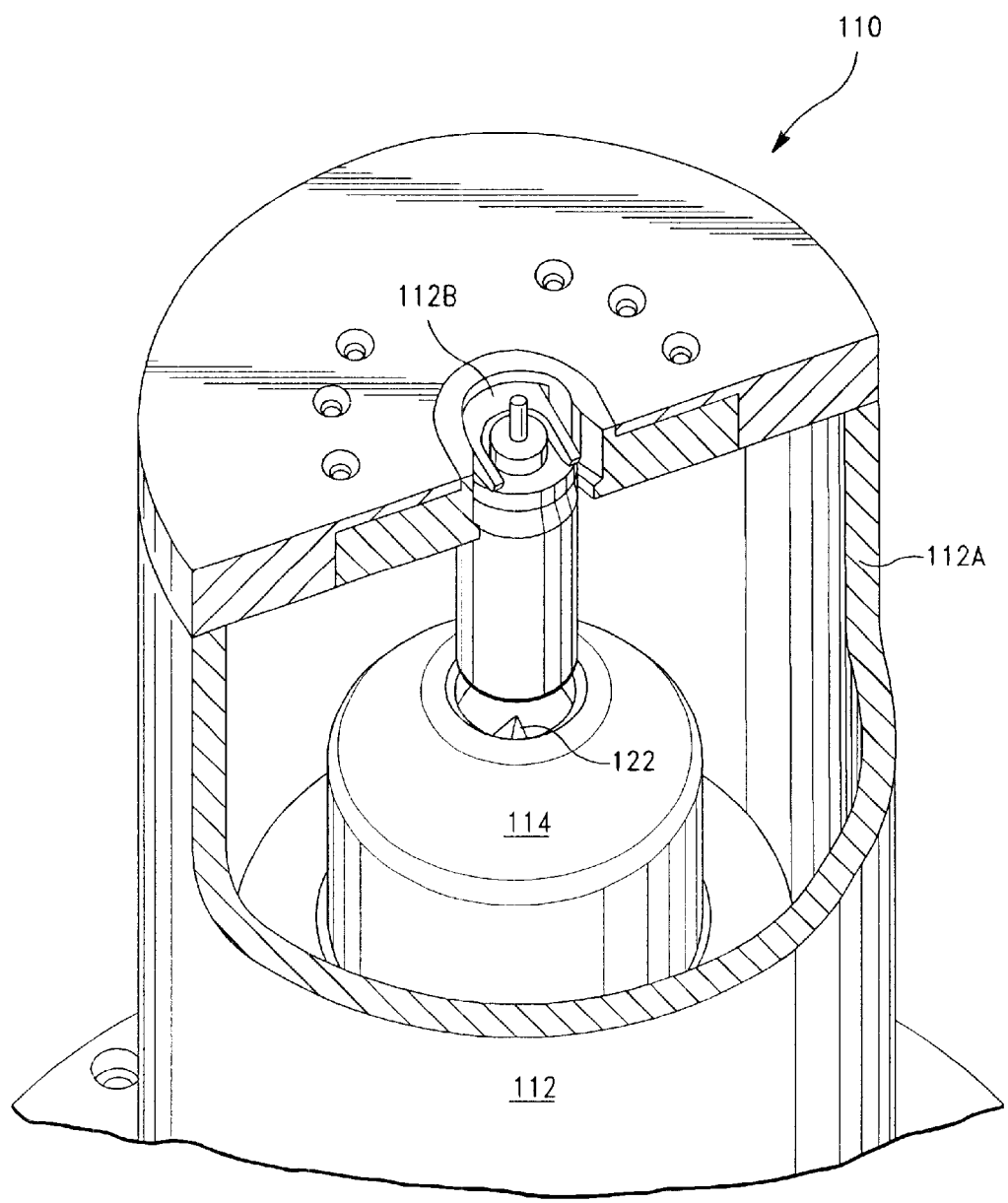
FIG. 4 is an enlarged view of the top portion of the extraction mechanism of the workstation shown in FIG. 3.

Applicants note that automated aerosol can content analyzer workstation 100 is preferably constructed by beginning with an open architecture ZYMARK® BENCHMATE II workstation manufactured by Zymark Corporation of Hopkinton, Mass., which is shown in phantom in FIGS. 2A and 2B. Applicant's workstation 100 is then designed around the ZYMARK® BENCHMATE II workstation by providing the extraction mechanism, collection receptacle, and additional computer controls that will be described hereinafter. In addition to the structural modifications provided to the ZYMARK® BENCHMATE II workstation, applicants' automated aerosol can content analyzer workstation 100 will utilize controlling software that has been designed specifically for workstation 100 and that comprises a VISUAL BASIC® user interface, and EXCEL® methods component and a ZYMARK® easy lab code component that will control workstation 100. The software utilized by workstation 100 may be developed by any software programmer skilled in the art and although applicants believe the software described above is preferred for use with applicants' workstation 100, applicants further believe that other software could be created that would also serve to control the hardware components of applicants' automated aerosol can content analyzer workstation 100.

The user interface software components of workstation 100 will provide a WINDOWS®—type user interface to enable the workstation operator to enter pertinent sample information prior to executing a testing run. The user interface must allow the user the ability to enter critical run information like product name, number of lots, number of cans per lot and delay start time from a single window. The program should provide the user with a convenient way to enter UV spectrophotometer response factor and response factor check information like standard number, standard weight, standard purity, and the standard expiration date. The control software will allow workstation 100 hardware to process intended aerosol can samples utilizing sets of predefined method parameters. As noted hereinbefore, although applicants have described preferred software for use with workstation 100, applicants believe that other software can be developed by one skilled in the art and would provide suitable interface with and control of workstation 100, and applicants intend such alternative software to be within scope of the present invention.

Further, applicants note that the preferred embodiment of workstation 100 will utilize a conventional 50-position aerosol can input rack, a conventional Easyfill module off-line sample storage device to store up to 50 HPLC samples and vials, and a conventional Easyfill rack which is a removable 50-position HPLC vial rack utilized by the Easyfill module. Additionally, workstation 100 will include a test tube rack capable of holding 50 test tubes for use in performing filtration, dilutions, and the like, and a standard rack capable of holding 10 test tubes for standard solution introduction into workstation 100. Workstation 100 further includes a vortex mixing module that is capable of mixing the contents of a test tube. All of these auxiliary components are a part of the base ZYMARK® BENCHMATE II workstation which applicants have modified as described herein in order to develop automated aerosol can content analyzer workstation 100. Applicants note, however, that workstation 100 can also suitably be designed and constructed as an original workstation apparatus without resorting to modification of an existing workstation. Both of the aforementioned embodiments of workstation 100 are intended to be within the scope of the invention.

Referring again to FIGS. 2–6 of the drawings, workstation 100 can be seen to include a robot (not shown) for engaging and transporting a selected aerosol can to and from workstation 100. An extraction station 110 is mounted on workstation 100 and comprises cylindrical housing 112 which defines a semi-cylindrical opening 112A at the top end thereof to allow the robot to deposit an aerosol can C in a U-shaped retainer element 112B (see FIG. 4) in the top of housing 112. U-shaped retainer element or clip 112B acts to releasably engage aerosol can C when aerosol can C is transported to extraction station 110 by the robot of automated aerosol can content analyzer workstation 100. Extraction station 110 further includes a vertically moveable extraction chamber 114 which has an aperture in the top thereof with a resilient O-ring 114A (see FIG. 5) seated therein. O-ring 114A serves to allow vertically moveable extraction chamber 114 to sealingly engage aerosol can C when extraction chamber 114 is caused to move from an inoperative mode beneath aerosol can C to a raised operative mode wherein aerosol can C is sealingly received within extraction chamber 114. Extraction chamber 114 is most suitably formed of LEXAN™ although other materials could be utilized to form the structure.

Figure 5:
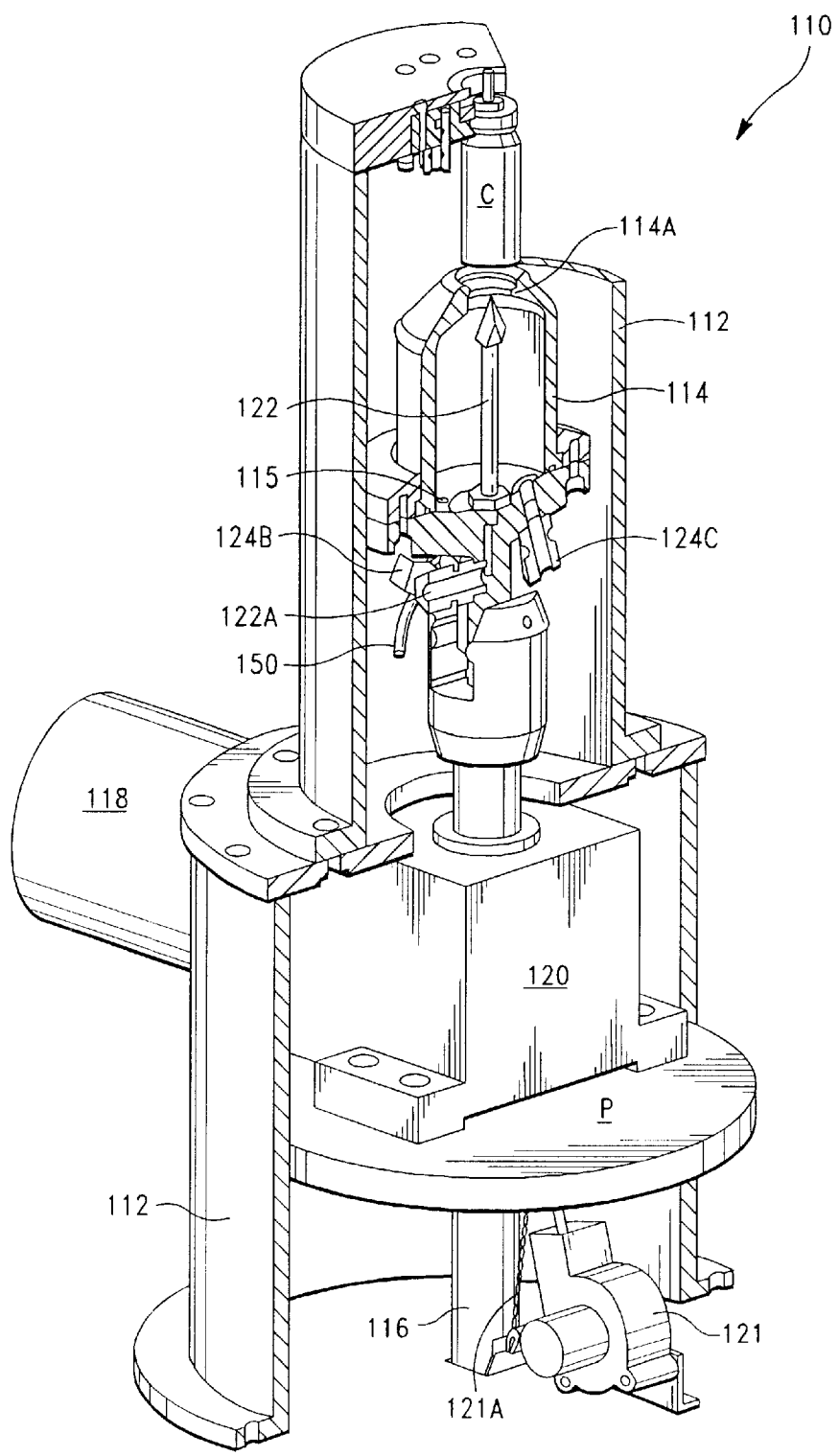
FIG. 5 is a vertical cross-sectional view of the extraction mechanism of the workstation shown in FIG. 3.
Figure 6B:
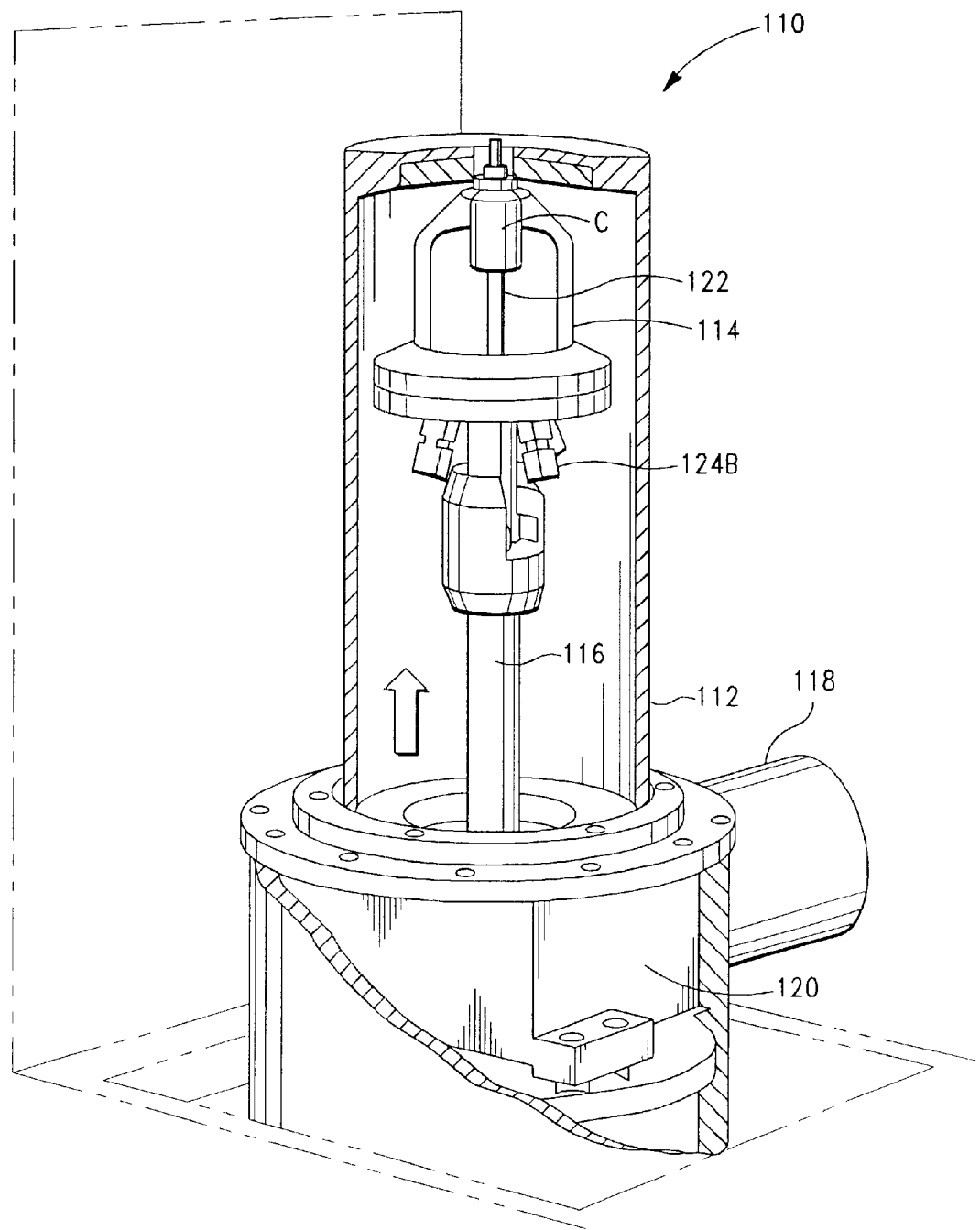
FIG. 6B is a perspective view of the extraction mechanism of the workstation shown in FIG. 3 with the extraction chamber elevated into its operative mode wherein an aerosol can has been sealingly received therein and pierced by the cannula of the extraction chamber.

As best seen in FIG. 5 of the drawings, extraction chamber 114 is vertically actuated by means of shaft 116 attached thereto which is motivated by stepper motor 118 through worm and gear drive 120. Stepper motor 118 is a Model No. 5RK606U-AMUL stepper motor manufactured by Oriental Motor of Los Angeles, Calif. (and stepper motor 118 is used with a linear head, Model No. 5LF1OU-1 from Oriental Motor). A distance transducer 121 is provided inside the bottom of housing 112 and in electrical connection with a suitably programmed computer (not shown but discussed in more detail hereinafter) to sense the vertical position of shaft 116 supporting extraction chamber 114. Distance transducer 121 comprises a spring-loaded wire cable 121A which is fed through a small pulley (not shown) mounted on the bottom of support plate P and beneath stepper motor 118. Wire cable 121A is attached at its free end to the bottom of vertical shaft 116 so that as shaft 116 moves up and down it reels wire cable 121 A in and out so as to cause distance transducer 121 to send a corresponding signal to the computer. Distance transducer 121 is preferably a UNIMEASURE Model No. LX-PA available from UniMeasure of Corvallis, Oreg.

Referring again to extraction chamber 114, cannula 122 can be seen to be fixedly mounted therein so as to extend co-axially upwardly and to terminate in an arrowhead-shaped punch head immediately beneath O-ring 114A. Cannula 122 is fluidly connected to solvent fluid pathway 122A which is in turn fluidly connected to a solvent source by means of a pump, tubing and solvent selection valves (not shown). Additionally, extraction chamber 114 is provided with three spray nozzles 124A–124C (124A not shown in drawings) which are directed upwardly and inwardly into extraction chamber 114. Spray nozzles 124A–124C are connected by three hose lines (not shown) which extend through a hole in the plate supporting stepper motor 118 and then out through a hole near the bottom of cylindrical housing 112 and then to a solvent selection valve (not shown) within the housing of workstation 100. The hose lines are connected at one end to spray nozzles 124A–124C and at the other end to the solvent selection valves (not shown) in workstation 100. Finally, extraction chamber 114 includes an extraction port 115, an extraction solution line 150, and a proportional valve 117 in communication therewith that is preferably located in the housing of workstation 100. According to the invention, the proportional valve 117 allows fluid from extraction chamber 114 to be drained therethrough in a controlled manner to be described hereinafter.

Automated aerosol can content analyzer workstation 100 further includes a fluid collection station 140, which includes glass flask 142 in fluid connection with proportional valve 117 of extraction chamber 114, as well as a mechanism (e.g., diluent line 152) for delivering one or more selected liquids to glass flask 142, a sampling line 154 for extracting one or more selected samples, an evac line 156 for extracting and/or discharging the remaining extraction solution from the flask 142, a weighing mechanism such as a mechanical or electronic analytical scale for determining when a predetermined target volume in glass flask 142 has been achieved, and a mixing mechanism 143 for mixing the contents of glass flask by means of a small paddle or similar mechanism. Workstation 100 includes a weighing mechanism (such as an analytical scale) for determining the full and empty weight of an aerosol can C when delivered thereto by the robot prior and subsequent to aerosol can content testing by workstation 100, and a mechanism for analyzing the drug content of an aerosol can from a sample taken from glass flask 142. The mechanism for analyzing the drug content of aerosol can C preferably includes on-line UV analysis with standard bracketing, dilution of samples, filtration, and off-line HPLC vial storage. Finally, workstation 100 includes a suitably programmed computer, preferably a personal computer such as an OPTIPLEX GXPRO, Model No. DCM, available from Dell Computer, for controlling the operation of workstation 100 by means of the user interface and control software described hereinbefore or by means of other suitable computer software.

Operation of Automated Aerosol Can Content Analyzer Workstation

As previously noted, the function of apparatus 100 is to determine the drug content of a selected aerosol can C in an automated manner and in accordance with government (e.g., FDA) regulations. Although other performance capabilities are certainly within the scope of the present invention, applicants contemplate that workstation 100 will function so as to have the capacity to process at least 25 aerosol cans C without operator intervention after the initial setup and will have a speed of processing of at least 10 cans per 2.50 hours. Thus, automated workstation 100 results in a significant reduction in operation time required for analyzing aerosol can contents.

Figure 1:
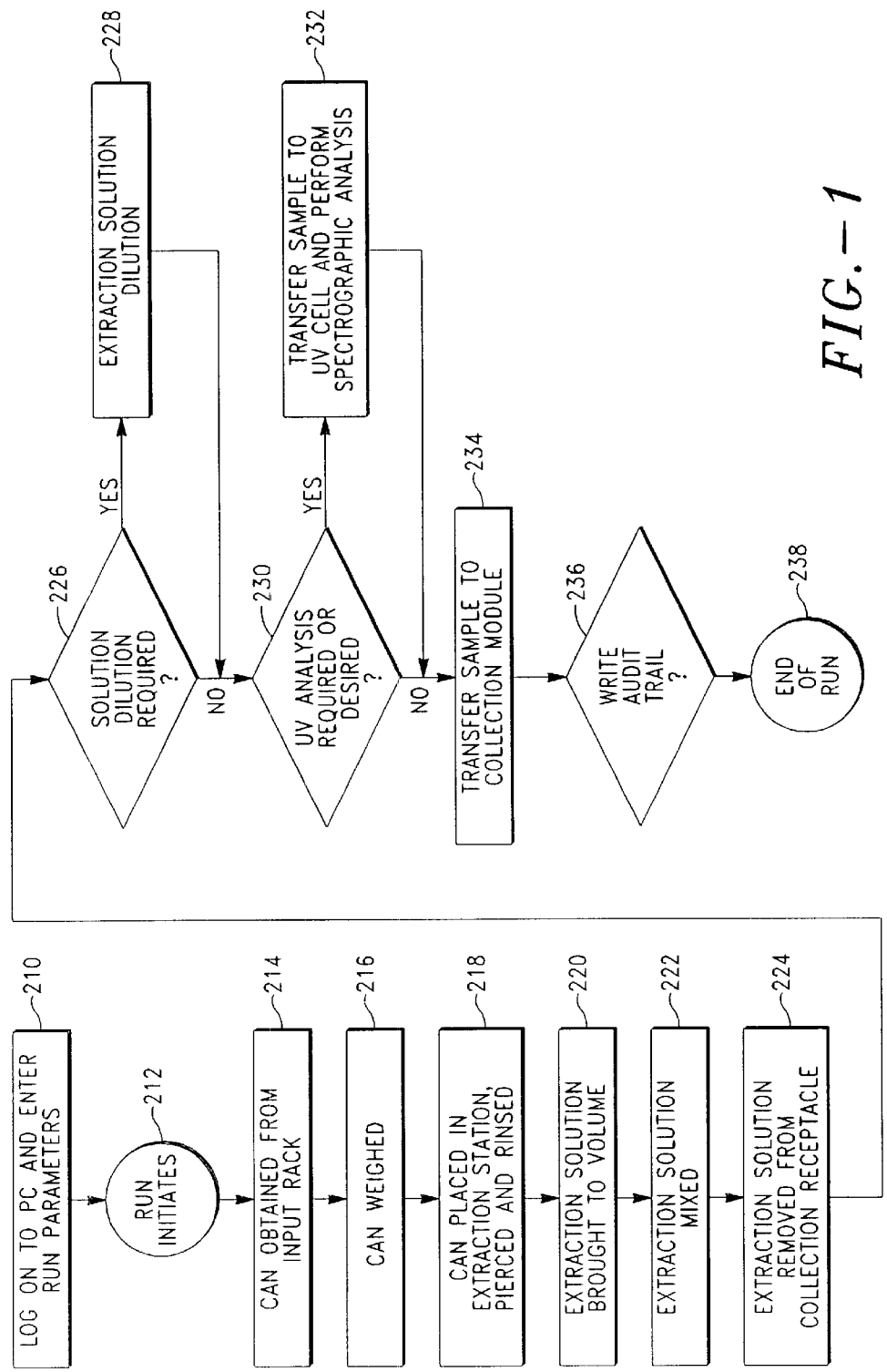
FIG. 1 is a process flow diagram illustrating the method of use of the automated aerosol can content analyzer workstation of the present invention.

With particular reference now to the FIG. 1 flow chart, applicants will now describe how to practice the method of the present invention with workstation 100. First of all, the user enters run information into a WINDOWS®—style graphical interface written in VISUAL BASIC® (Box 210). The relevant run parameters are then downloaded to the robotic system by a serial link when the user initiates the actual run (Box 212). The robot obtains aerosol can C from the 50-position input rack (Box 214) and weighs it on an analytical balance (Box 216). The robot then removes the aerosol can C from the analytical balance and places it into U-shaped retainer element 112B of extraction station 110 (Box 218). Once aerosol can C is releasably positioned in extraction station 110, extraction chamber 114 is motivated by stepper motor 118 so as to move from an inoperative mode beneath aerosol can C (see FIG. 6A) to an elevated operative mode wherein aerosol can C is sealingly received by O-ring 114A of extraction chamber 114 (see FIG. 6B) and aerosol can C is pierced by the arrowhead-shaped punch head of cannula 122 so as to leave a large hole in the bottom of aerosol can C.

The pressurized contents of aerosol can C are expelled into extraction chamber 114, and the resulting pressure is allowed to slowly bleed through the proportional valve 117 which is in fluid communication with collection flask 142. Once the pressure of extraction chamber 114 and flask 142 equalize, the residual drug product and propellant therein is rinsed from the inside of aerosol can C by pumping a suitable solvent (e.g., methanol) and/or air through cannula 122. The resulting extraction solution is then delivered to collection flask 142 through the extraction line 150 and proportional valve 117. Simultaneously, the inner surface of extraction chamber 114 is rinsed with solvent (e.g., methanol) through three spray nozzles 124A–124C mounted in the bottom of extraction chamber 114. The resulting extraction solution is then also delivered to collection flask through the proportional valve 117. Once the extraction is complete, the robot manipulates aerosol can C to obtain the empty weight and then returns it to the input rack.

The extraction solution in collection flask 142 is then brought to a target volume (Box 220) gravemetrically by collection station 140 utilizing the feedback of an analytical balance and an integrated liquid delivery system (i.e., diluent line 152) in collection station 140. Next, the extraction solution is mixed (Box 222) so as to be homogeneous by a motor-driven mixing mechanism 143 provided by collection station 140. The final extraction solution is then removed from glass flask 142 either by syringe or via sampling line 154 and workstation 100 (Box 224) makes any necessary dilutions (Box 226 and Box 228) and delivers the solution to an HPLC vial in an Easyfill fraction collector (Box 234) or analyzes the solution utilizing a UV spectrophotometer equipped with a flow-through cell (Box 230 and Box 232), which is in liquid communication with sample line 154, prior to delivering the solution to the HPLC vial in the Easyfill fraction collector (Box 234). Any remaining extraction solution can then be discharged via evac line 156. The last step performed (Box 236) before processing the next aerosol can C is to write an audit trail of the data collected from balance operations along with other run information to an EXCEL® file. The end of the run (Box 238) has now been achieved and a new run can be initiated on workstation 100 as desired.

It will be appreciated that the precise sequences and times set forth above have been found to be desirable. However, applicants have described the sequences and times only as an illustration of one embodiment of the method of the present invention and do not intend to be limited thereby since numerous variations of the sequences and times are possible and within the intended scope of applicants' invention as set forth in the appended claims. Further, as noted above, although applicants' invention as described herein is a modification of a ZYMARK® BENCHMATE II workstation available from Zymark Corporation, applicants do not intend to be limited thereto since it is possible to construct the apparatus of the present invention in other ways, and applicants intend all embodiments of the apparatus and method of the present invention to be within the intended scope of applicants' invention as set forth in the appended claims.

The application of which this description and claims form part may be used as a basis for priority in respect of any subsequent application. The claims of such subsequent application may be directed to any feature or combination of features described herein. They may take the form of product, composition, process or use claims and may include, by way of example and without limitation, one or more of the following claims.

It will be understood that various details of the invention may be changed without departing from the scope of the invention. Furthermore, the foregoing description is for the purpose of illustration only, and not for the purpose of limitation—the invention being defined by the claims.

What is claimed is:

1. A constituent extraction system for an aerosol can content analyzer workstation, comprising:
    (a) an extraction chamber for receiving an aerosol can therein, said aerosol can having an internal chamber containing a constituent;
    (b) a piercing element positioned within said extraction chamber for piercing said aerosol can when said can is at ambient temperature, said piercing element including at least one first spray nozzle for delivering an extraction medium within said aerosol can internal chamber to extract said constituent;
    (c) a collection receptacle in fluid communication with said extraction chamber for collecting said extraction medium and said constituent; and
    (d) at least one second spray nozzle disposed in said collection receptacle to deliver a rinsing fluid therein, said first and second spray nozzle being adapted to substantially simultaneously deliver said extraction medium and said rinsing fluid.

2. The extraction system according to claim 1, wherein said rinsing fluid comprises a solvent.

3. The extraction system according to claim 2, wherein said solvent comprises methanol.

4. The extraction system according to claim 1, wherein three second spray nozzles are disposed in said extraction chamber, said second nozzles being positioned in the bottom of said extraction chamber so as to direct said rinsing fluid generally upwardly into said extraction chamber.

5. The extraction system according to claim 1, wherein said extraction medium comprises a solvent.

6. The extraction system according to claim 5, wherein said solvent comprises methanol.

7. The extraction system according to claim 1, wherein said collection receptacle comprises a glass flask.

8. The extraction system according to claim 1, wherein said collection receptacle further includes at least one sampling port to withdraw a selected sample volume from said collection receptacle.

9. The extraction system according to claim 1, further including a valve fluidly connecting said extraction chamber and said collection receptacle.

10. The extraction system according to claim 9, wherein said valve comprises a proportional valve.

11. The extraction system according to claim 1, further including a liquid delivery system for delivering at least one selected rinsing fluid to said collection receptacle.

12. The extraction system according to claim 1, further including a volume detection mechanism disposed in said collection receptacle.

13. The extraction system according to claim 1, further including an agitator for mixing the contents of said collection receptacle.

14. The extraction system according to claim 1, further including a housing having an engagement mechanism for engaging an aerosol can placed therein.

15. The extraction system according to claim 14, wherein said engagement mechanism comprises a substantially U-shaped clip.

16. The extraction system according to claim 14, wherein said extraction chamber defines a can receiving aperture for receiving an aerosol can in a pressure sealed fashion and said housing is positioned on said content analyzer workstation such that a can held by said engagement mechanism can be received within said aperture when said housing and said extraction chamber are moved from a first position distanced from each other to a second position closer to each other.

17. The extraction system according to claim 16, wherein a resilient O-ring is mounted in said aperture of said extraction chamber.

18. The extraction system according to claim 16, wherein said housing is positioned above said extraction chamber and said engagement mechanism of said housing is aligned with said receiving aperture of said extraction chamber such that a can engaged in said engagement mechanism is received with said receiving aperture when said housing and said extraction chamber are brought to said second position.

19. The extraction system according to claim 18, further including an actuator and transducer in operative association with either said extraction chamber or said housing for motivating said extraction chamber and said housing from said first position to said second position.

20. The extraction system according to claim 19, wherein said actuator comprises a stepper motor with a worm and gear drive and said transducer comprises a linear transducer.

21. The extraction system according to claim 19, wherein said actuator and said transducer generate at least one signal to identify said relative positions of said housing and said extraction chamber.

22. The extraction system according to claim 1, wherein said piercing element comprises a cannula disposed proximate the bottom of said extraction chamber.

23. The extraction system according to claim 1, further including a first analyzer for evaluating the constituent contained in said aerosol can.

24. The extraction system according to claim 23, wherein said first analyzer includes means for determining the amount of drug content of said constituent by either UV or HPLC testing.

25. The extraction system according to claim 1, further including a robot for engaging and moving aerosol cans to be received by said extraction chamber.

26. The extraction system according to claim 1, further including a release valve in fluid communication with said extraction chamber for releasing the pressure therefrom in a controlled fashion.

27. The extraction system according to claim 1, further including a weighing mechanism for determining the weight of an aerosol can before and after piercing by said piercing element.

28. The extraction system according to claim 27, wherein said weighing mechanism comprises a analytical balance.

29. The extraction system according to claim 1, further including a computer for controlling the operation of said can content analyzer workstation in accordance with selected performance parameters and for collecting selected data during operation of said workstation.

30. The extraction system according to claim 29, wherein said computer comprises a personal computer.

31. An automated aerosol can content analyzer workstation comprising:
    (a) an extraction mechanism mounted on the workstation and comprising:
        (i) a housing having an engagement mechanism in the top thereof for releasably engaging an aerosol can;
        (ii) a vertically moveable extraction chamber with an aperture defined in the top thereof for sealingly receiving an aerosol can therein when the extraction chamber is moved upwardly from an inoperative mode beneath an aerosol can engaged by the housing engagement mechanism to an elevated operative mode, and a cannula fixedly mounted within the extraction chamber so as to rupture an aerosol can engaged by the housing engagement mechanism when the extraction chamber is moved upwardly from the inoperative mode to the elevated operative mode to allow the contents of a pierced aerosol can to be expelled from a ruptured can into the extraction chamber of the extraction mechanism and to then deliver a rinsing fluid through the cannula into an aerosol can;

(iii) one or more spray nozzles in fluid communication with the extraction chamber for rinsing the inside of the extraction chamber of the extraction mechanism with rinsing fluid;

(b) a collection receptacle in fluid connection with the extraction chamber for receiving fluid from the extraction chamber;

(c) an analyzing mechanism for determining the aerosol content of an aerosol can from a sample taken from the collection receptacle; and (d) a computer for controlling the operation of the automated aerosol can content analyzer workstation in accordance with selected performance parameters and for collecting selected data during operation of the aerosol content workstation.

32. The automated aerosol can content analyzer workstation according to claim 31, wherein the engagement mechanism in the top of the extraction mechanism housing comprises a U-shaped clip.

33. The automated aerosol can content analyzer workstation according to claim 31, wherein a resilient O-ring is mounted in the aperture of the extraction chamber for sealingly engaging an aerosol can.

34. The automated aerosol can content analyzer workstation according to claim 31, wherein the cannula is mounted to the bottom of the extraction chamber and extends upwardly within the extraction chamber and terminates beneath the aperture in the top thereof.

35. The automated aerosol can content analyzer workstation according to claim 31, wherein the rinsing fluid delivered through the cannula is a solvent.

36. The automated aerosol can content analyzer workstation according to claim 31, wherein the one or more spray nozzles comprises 3 spray nozzles mounted in the bottom of the extraction chamber so as to direct a rinsing fluid generally upwardly into the extraction chamber.

37. The automated aerosol can content analyzer workstation according to claim 36, wherein the rinsing fluid comprises a solvent.

38. The automated aerosol can content analyzer workstation according to claim 31, including a robot for engaging and transporting an aerosol can to and from the aerosol content analyzer workstation.

39. The automated aerosol can content analyzer workstation according to claim 31, including a valve for allowing fluid within the extraction chamber to be drained therefrom.

40. The automated aerosol can content analyzer workstation according to claim 31, including an actuator and transducer in operative association with the extraction chamber for vertically motivating the extraction chamber from the inoperative mode to the operative mode and generating a signal corresponding to the relative position of the extraction chamber.

41. The automated aerosol can content analyzer workstation according to claim 31, including a weighing mechanism for determining the full and empty weight of an aerosol can from a sample taken from the collection receptacle.

42. A method for analyzing the drug content of an aerosol can comprising the steps of:

(a) placing the aerosol can in an extraction chamber wherein said extraction chamber is at ambient temperature; and (b) rupturing the aerosol can so as to allow the pressurized contents of the aerosol can to expel into the extraction chamber and then analyzing the contents of the aerosol can.

43. The method for analyzing the drug content of an aerosol can according to claim 42, including collecting the contents of the can in a remote vessel.

44. The method for analyzing the drug content of an aerosol can according to claim 43, including analyzing the contents of the aerosol can by analyzing a portion of the contents collected in the remote vessel.

45. The method for analyzing the drug content of an aerosol can according to claim 42, including rinsing the inside of the aerosol can and extraction station with a solvent, collecting a solution of the solvent and the contents of the can in a remote vessel, and analyzing the solution collected in the remote vessel.

46. The method for analyzing the drug content of an aerosol can according to claim 42, including allowing the pressure of the extraction chamber to be released in a controlled manner, collecting the contents of the aerosol can in a remote vessel, and analyzing the contents collected in the remote vessel.

47. A method for analyzing the drug content of an aerosol can with an automated workstation, comprising the steps of:

(a) entering selected performance parameters into a computer control operatively associated with the workstation;

(b) robotically selecting a selected aerosol can from an input rack or the like and weighing the aerosol can and then delivering the aerosol can to an extraction mechanism of the workstation wherein the aerosol can is releasably engaged in a stationary position above a vertically moveable extraction chamber having an upwardly extending cannula therein;

(c) rupturing the aerosol can by causing the vertically moveable extraction chamber to move from an inoperative mode beneath the aerosol can to an elevated operative mode wherein the aerosol can is sealingly engaged by the extraction chamber and ruptured by the cannula thereof so as to allow the pressurized contents of the aerosol can to expel into the extraction chamber;

(d) allowing the pressurized contents of the extraction chamber to bleed through a proportional valve in fluid connection with the extraction chamber and to be delivered to a collection flask;

(e) rinsing the inside of the aerosol can by pumping a solvent through the cannula within the aerosol can and allowing the solvent to collect in the extraction chamber and to then be delivered to the collection flask through the proportional valve;

(f) spraying a solvent rinse into the inside of the extraction chamber with one or more spray nozzles in fluid communication therewith and then delivering the solvent to the collection flask through the proportioning valve;

(g) robotically delivering the empty aerosol can to a scale to determine the empty aerosol can weight and returning the empty aerosol can to the input rack or other selected collection site; and (h) analyzing a portion of the extraction solution to determine the aerosol content of the aerosol can.

48. The method for analyzing the drug content of an aerosol can according to claim 47, including pumping air through the cannula in addition to the solvent to rinse the inside of the aerosol can.

49. The method for analyzing the content of an aerosol can according to claim 47, including sensing the relative vertical position of the extraction chamber during movement thereof and generating a corresponding signal to the computer control of the workstation.

50. The method for analyzing the content of an aerosol can according to claim 49, including sensing the relative vertical position of the extraction chamber with a linear transducer operatively associated with the extraction chamber.

* * * * *